United States Patent
Jackman et al.

(10) Patent No.: US 8,701,669 B2
(45) Date of Patent: Apr. 22, 2014

(54) NASAL CANNULA POSITIONING DEVICE

(76) Inventors: Robert L. Jackman, Frankfort, IL (US); Kimberly J. Anderson, Mukwonago, WI (US)

(*) Notice: Subject to any disclaimer, the term of this patent is extended or adjusted under 35 U.S.C. 154(b) by 0 days.

(21) Appl. No.: 13/597,743

(22) Filed: Aug. 29, 2012

(65) Prior Publication Data

US 2013/0092174 A1    Apr. 18, 2013

Related U.S. Application Data

(60) Provisional application No. 61/548,270, filed on Oct. 18, 2011.

(51) Int. Cl.
*A61M 16/06* (2006.01)

(52) U.S. Cl.
USPC .................. 128/207.18; 128/207.11

(58) Field of Classification Search
USPC ............ 128/206.27, 207.11, 207.13, 207.17, 128/207.18, DIG. 26; 450/82, 86; 2/323–335; 24/442–453
See application file for complete search history.

(56) References Cited

U.S. PATENT DOCUMENTS

| | | | | |
|---|---|---|---|---|
| 4,665,566 A | * | 5/1987 | Garrow | 2/171 |
| 4,739,757 A | * | 4/1988 | Edwards | 128/207.18 |
| 4,836,200 A | * | 6/1989 | Clark | 128/207.18 |
| 5,284,469 A | * | 2/1994 | Jasen et al. | 602/17 |
| 5,362,303 A | * | 11/1994 | Jasen et al. | 602/17 |
| 5,368,024 A | * | 11/1994 | Jones | 128/207.17 |
| 5,653,228 A | * | 8/1997 | Byrd | 128/207.11 |
| 5,704,916 A | * | 1/1998 | Byrd | 604/179 |
| 6,899,102 B1 | * | 5/2005 | McGlothen | 128/207.18 |
| 2002/0139372 A1 | * | 10/2002 | Shikani | 128/207.17 |
| 2005/0188993 A1 | * | 9/2005 | Steeves et al. | 128/207.17 |
| 2012/0285471 A1 | * | 11/2012 | Keesy | 128/207.18 |

* cited by examiner

*Primary Examiner* — Justine Yu
*Assistant Examiner* — Valerie L Skorupa
(74) *Attorney, Agent, or Firm* — Andrus Intellectual Property Law, LLP

(57) ABSTRACT

An apparatus for securing a nasal cannula comprising a pair of oxygen tube holders connected via a strap, the nasal cannula securing device being positionable behind the head of a patient and slightly below the patient's ears so as to secure the nasal cannula in place.

12 Claims, 2 Drawing Sheets

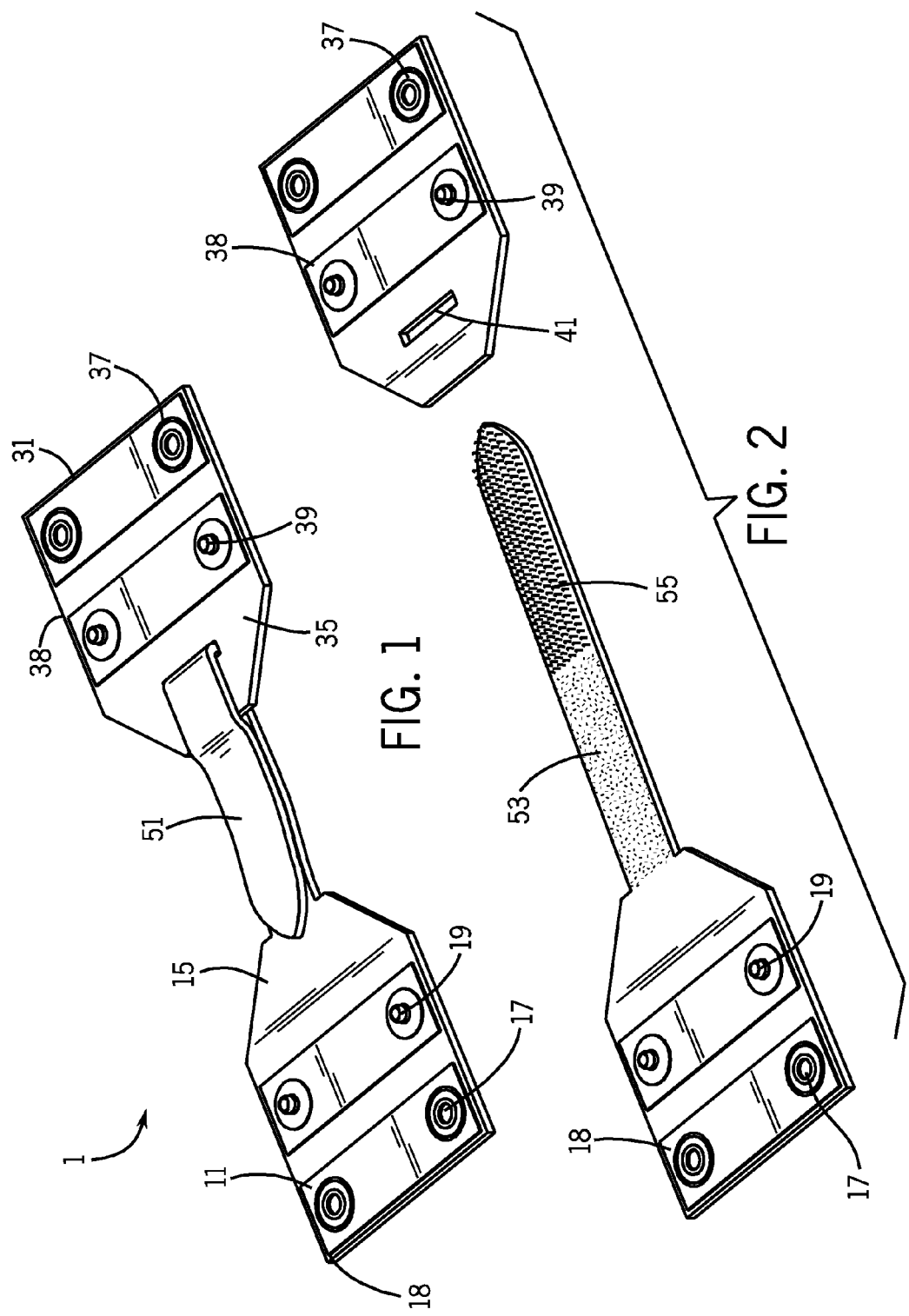

NASAL CANNULA POSITIONING DEVICE

PRIORITY CLAIM

This application claims the benefit and priority of U.S. Provisional Patent Application No. 61/548,270 filed Oct. 18, 2011.

FIELD OF THE INVENTION

The present invention relates generally to devices for securing the position of nasal cannula in the nostrils of a user. More specifically, the present invention is directed to an elastic strap device designed to secure a nasal cannula by securing the oxygen tubes attached to the cannula in place behind the head of a patient.

BACKGROUND OF THE INVENTION

Various physical conditions require an increased oxygen supply to a patient. In severe cases, an oxygen mask may be required. However, in less severe cases, an oxygen mask is not required, and the increased oxygen flow is provided by a nasal cannula connected to oxygen tubes. The nasal cannula is generally worn in or near the entry to the nasal passages.

Generally speaking, when in use, a nasal cannula is simply draped over one ear, positioned underneath the nose, and then draped over the other ear. While satisfactory for completely immobile individuals, frequently, when a nasal cannula is installed over the ears of a patient, it becomes dislodged. This is particularly likely to occur when the person is asleep and is typically caused by tossing and turning of the person causing contact of the cannula and cannula tube against the bed and bedclothes. The person generally is wakened when the cannula dislodges or falls from the person's nose due to the insufficient supply of oxygen to the person's brain, and the person must subsequently reattach the cannula. This activity disrupts the person's sleep and frequently occurs several times each night. If the person does not wake, potentially serious hypoxia and resulting in permanent brain damage and death can occur due to the lack of sufficient oxygen supply to the person's brain.

Additionally, even when the nasal cannula is properly positioned, the nasal securing device disclosed herein ensures more consistent oxygen intake by the patient, which is beneficial to the patient. Also beneficial is that the nasal cannula securing device improves the ability of a pulmonologist to accurately evaluate a patient's oxygen requirements.

A further advantage can result from use in the normal hospital environment. Normally, with a patient in the hospital, with the exception of an intensive care facility, the attending nurses have multiple patients and it is next to impossible to monitor every patient's nasal cannula and to verify that there is complete and consistent insertion of the prongs in the nostrils. Use of the present invention in the hospital environment is likely to reduce the need to continuously monitor and reinstall a patient's nasal cannula. The improved flow of oxygen from a consistently placed nasal cannula may even reduce patient hospital stays and improve patient quality of life.

Thus, there is a need for a means and method for retaining a cannula in place during use. It is clear therefore that a need exists for a device to secure a nasal cannula to a patient's head in a light, inexpensive, and effective manner, and to do so in a manner that will be unobtrusive to the patient.

SUMMARY OF THE INVENTION

In view of the foregoing, what is needed is an improved nasal cannula positioning device that is comfortable to wear and that ensures a consistent flow of oxygen to the patient. The disclosed invention provides just such a nasal cannula positioning device.

More specifically, the nasal cannula positioning device is comprised of an adjustable-length Velcro strap further comprised of an oxygen tube retainer on each end. Each oxygen tube retainer is generally comprised of an elastic material and at least one fastening device, such as a snap closure. The elastic material is essentially folded around the cannula and then snapped to itself.

In use, the positioning device is employed to secure the nasal cannula as it normally would be used, that is, the oxygen tube is draped over one ear, positioned underneath the nose, and then draped over the other ear. In summary, the disclosed nasal cannula positioning device provides a simple device to more effectively keep the cannula in the nostrils of a patient. This is accomplished by securing the cannula tubes behind the head of a patient such that the positioning device is most preferably approximately level with the center of the patient's ears. This positioning arrangement creates a slight tension in the cannula tube thereby securing the cannula in the nostrils of a patient.

BRIEF DESCRIPTION OF THE DRAWINGS

FIG. 1 is a top and side perspective view of the nasal cannula positioning device laid flat so as to show the snap enclosure used for the cannula retainers.

FIG. 2 is a top and side perspective view of the nasal cannula positioning device showing the length adjustment means.

DETAILED DESCRIPTION OF THE INVENTION

Figure 3:
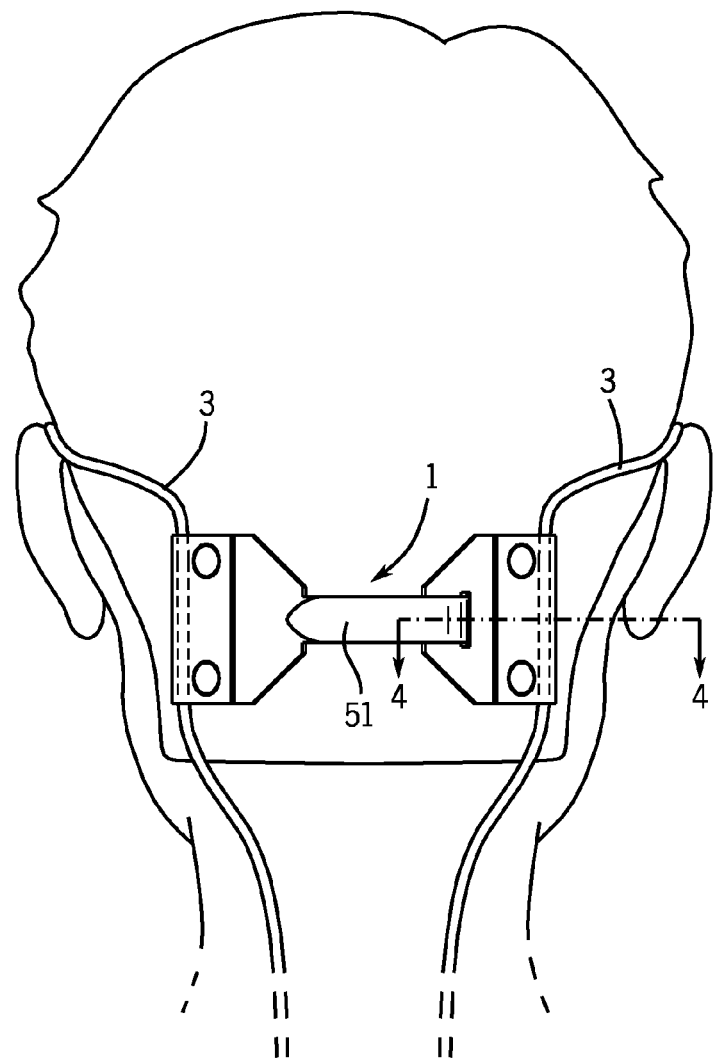
FIG. 3 is a rear elevational view of the nasal cannula positioning device wherein the oxygen tubes are looped over the ears of a patient as would normally be the case when used in connection with a patient.

Now referring to the drawings in detail wherein like numbers refer to like elements throughout, FIG. 1 shows the nasal cannula positioning device 1 comprising an adjustable strap 51 and oxygen tube holders 11, 31 at each end of the adjustable strap 51. As also shown in FIG. 2, each of the oxygen tube holders 11, 31 is further comprised of fasteners 18, 38.

Many different fasteners could be used and the type of fastener employed is not a limitation of this invention. Referring again to FIG. 1, snap fasteners 18, 38 are preferred for their ease of use. One preferred embodiment of the invention comprises a pair of snap fasteners 18, 38 on each oxygen tube holder 11, 31. Such snap fasteners 18, 38 comprise a female fastener end 17, 37 and a male fastener end 19, 39.

Referring to FIG. 3, when a patient is on five (5) or less liters of oxygen, the nasal cannula tubes 3, 5 have a diameter of approximately 3.2 mm. For patients who require more than five (5) liters of oxygen, the nasal cannula tubes 3, 5 diameter are approximately 4 mm. Therefore, it is particularly important that the material used for the oxygen tube holders 11, 31, (see FIG. 1) and specifically the first portions 13, 33, which are shown in FIG. 2, have some degree of elasticity such that they can accommodate both oxygen tube sizes.

Referring to FIG. 1, each of the oxygen tube holders 11, 31 are further comprised of a second portion 15, 35. The second portion 15 of the first oxygen tube holder 11 is further comprised of a strap 51. As shown in FIG. 2, the strap 51 is comprised of a first portion 53 comprising a loop material and a second portion 55 comprising complementary hook material. The second portion 35 of the second oxygen tube holder 31 further comprises an aperture 41. Now referring to FIG. 1, the second oxygen tube holder 31 is attachable to the first oxygen tube holder 11 by looping the strap 51 through the aperture 41 in the second portion 35 of the second oxygen tube holder 31 back over itself.

Now referring to FIG. 3, which shows a back elevational view of a patient's head showing the the nasal cannula positioning device 1. As shown, the nasal cannula position device 1 is preferably positioned at the back of patient's head, just below the patient's ears. In this way, the first oxygen tube 3 and the second oxygen tube 5 can drape, as per usual, over the ears of a patient, but instead of curling around the bottom of a patient's ears, be secured behind the head of a patient.

Figure 4:
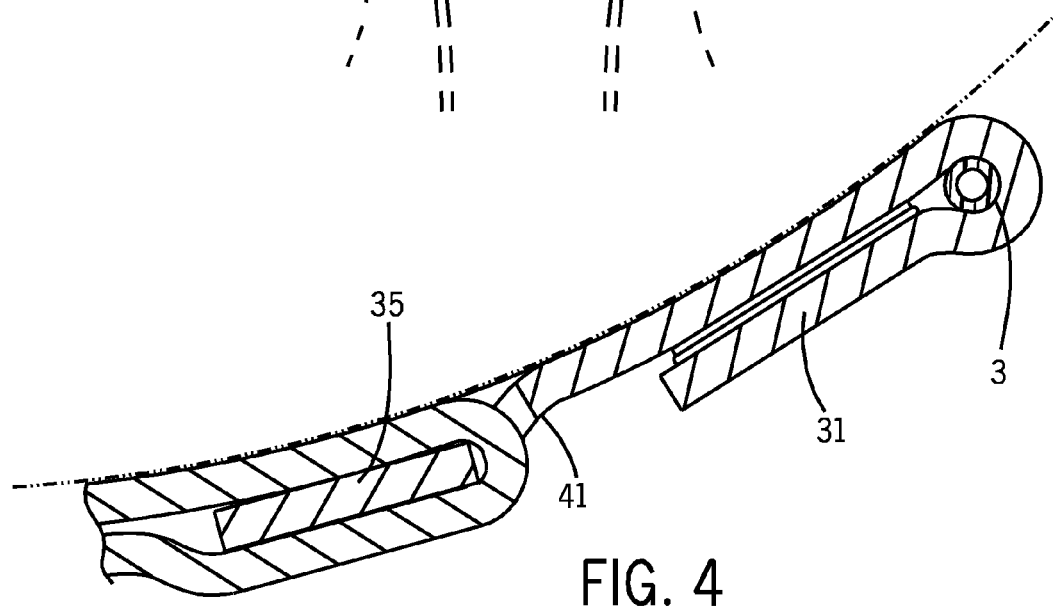
FIG. 4 is a cross-sectional view of the nasal cannula positioning device shown in FIG. 3 showing the oxygen tube within the enclosure means.

FIG. 4 shows a cross-sectional view of the second oxygen tube holder 31 with the fastener (not shown) secured around the first oxygen tube 3. FIG. 4 also shows the strap 51 fitted through the aperture 41 in the second portion 35 of the tube holder 31. As shown most clearly in FIG. 4, friction between the first oxygen tube 3 and the elastic material of the oxygen tube holder 31 permits adjustment of cannula tube 3 within the oxygen tube holder 31, but otherwise restrains slippage of the cannula tube 3.

In practice, the nasal cannula positioning device 1 of the disclosed invention is initially installed on the oxygen tubes 3, 5 which allows the elastic material of the oxygen tube holders 11, 31 to be slightly stretched around the oxygen tubes 3, 5, which permits easier engagement for the fasteners 18, 38. Generally speaking, the strap 51 between the oxygen tube holders 11, 31 is left unattached such that the cannula (not shown) and oxygen tubes 3, 5 can be accurately positioned on a patient. At that time, either the patient or a second person can move the oxygen tube holders 11, 31 upwardly along the cannula to approximately the bottom of the patient's ears. Next, the strap 51 is inserted through the aperture 41 in the second portion 35 of the second oxygen tube holder 31 to connect the ends of the oxygen tube holders 11, 31 to one another. At that point, the oxygen tube holders 11, 31 are moved upwardly along the cannula tubes 3, 5 to restrain the prongs of the cannula comfortably in the nose of the patient. The inventor has found that when the cannula tube retainers 11, 31 are located approximately at the middle of the ears, the cannula is comfortably positioned in the nose of the patient.

After the initial installation, a more expedient method can be used for removal and installation of the nasal cannula positioning device 1. First, the prongs of the cannula (not shown) can be gently removed from the patient's nostrils and pulled over the patient's head. Then, the strap 51 can be loosened so as to maximize the distance between the oxygen tube holders 11, 31. At this point, the entire cannula tube 11 can be easily removed. The cannula can then be replaced by repositioning the cannula in the nose, replacing the oxygen tubes 3, 5 over the ears of the patient and then readjusting the oxygen tube holders 11, 31 along the oxygen tubes 3, 5 to tighten the cannula prongs into the nostrils of the patient. In summary then, there are three ways to easily remove the cannula and nasal cannula positioning device 1: undo the fasteners 18, 38 and remove the nasal cannula positioning device 1; undo the strap 51 and remove the oxygen tubes 3, 5; or slide the oxygen tube holders 11, 31 far enough along the oxygen tubes 3, 5 so that the cannula and the nasal cannula positioning device can be removed.

Additional advantages and modifications will readily occur to those skilled in the art. Therefore, the invention in its broader aspects is not limited to the specific details disclosed and described herein.

The invention claimed is:

1. An apparatus for securing a nasal cannula across a patient's face, the apparatus comprising:
    a first oxygen delivery tube connected to the nasal cannula,
    a second oxygen delivery tube connected to the nasal cannula:
    a first oxygen delivery tube holder comprising an elastic material, the elastic material being looped over itself to frictionally retain the first oxygen delivery tube and being securable to itself by a fastener, wherein elastic material of the first oxygen delivery tube holder allows the first oxygen delivery tube holder to both slide along a length of the first oxygen delivery tube and accommodate varying diameters of the first oxygen delivery tube;
    a second oxygen delivery tube holder comprising an elastic material, the elastic material being looped over itself to frictionally retain the second oxygen delivery tube and being securable to itself by a fastener, wherein elastic material of the second oxygen delivery tube holder allows the second oxygen delivery tube holder to both slide along a length of the second oxygen delivery tube and accommodate varying diameters of the second oxygen delivery tube; and
    a strap attached to the first oxygen delivery tube holder, the strap being adjustable in length and selectively attached to the second oxygen delivery tube holder to adjust the distance between the first and second oxygen delivery holders.

2. The apparatus of claim 1 wherein the strap further comprises a first portion comprising loop material and a second portion comprising complimentary hook material and the second oxygen delivery tube holder comprises an aperture and the first oxygen delivery tube holder is securable to the second oxygen delivery tube holder by pulling the strap through the aperture in the second oxygen delivery tube holder and attaching the second portion of the strap to the first portion of the strap using the complimentary hook and loop material.

3. The apparatus of claim 2 wherein the strap is adjustable in length by overlapping more or less of the complimentary hook and loop material.

4. The apparatus of claim 1 wherein the fastener used to create a loop in the first oxygen delivery tube holder and the second oxygen delivery tube holder is a snap fastener.

5. The apparatus of claim 1 wherein the fastener used to create a loop in the first oxygen delivery tube holder and the second oxygen delivery tube holder is complimentary hook and loop material.

6. The apparatus of claim 1 wherein the strap further comprises a first portion comprising loop material and a second portion comprising complimentary hook material and the second oxygen delivery tube holder comprises an aperture and the first oxygen delivery tube holder is securable to the second oxygen delivery tube holder by pulling the strap through the aperture in the second oxygen delivery tube holder and attaching the second portion of the strap to the first portion of the strap using the complimentary hook and loop material.

7. The apparatus of claim 6 wherein the strap is adjustable in length by overlapping more or less of the complimentary hook and loop material.

8. An apparatus for securing a nasal cannula across a patient's face, the nasal cannula comprising a nasal insert, the apparatus comprising:
- a first oxygen delivery tube connected to the nasal cannula and positionable on a first side of the patients face;
- a second oxygen delivery tube connected to the nasal cannula and positionable on a second side of the patient's face;
- a first oxygen delivery tube holder comprising an elastic material, the elastic material being looped over itself to frictionally retain the first oxygen delivery tube and being securable to itself by a fastener, wherein elastic material of the first oxygen delivery tube holder allows the first oxygen delivery tube holder to both slide along a length of the first oxygen delivery tube and accommodate varying diameters of the first oxygen delivery tube;
- a second oxygen delivery tube holder comprising an elastic material, the elastic material being looped over itself to frictionally retain the second oxygen delivery tube and being securable to itself by a fastener, wherein elastic material of the second oxygen delivery tube holder allows the second oxygen delivery tube holder to both slide along a length of the second oxygen delivery tube and accommodate varying diameters of the second oxygen delivery tube;
- a strap attached to the first oxygen delivery tube holder, the strap being adjustable in length and selectively attached to the second oxygen delivery tube holder to adjust the distance between the first and second oxygen delivery holders.

9. The apparatus of claim 8 wherein the fastener used to create a loop in the first and second cannula retainers is a snap fastener.

10. The apparatus of claim 8 wherein the fastener used to create a loop in the first and second cannula retainers is complimentary hook and loop material.

11. The apparatus of claim 8 wherein the strap is positionable behind the patient's head and below the patients ears such that the strap affixes the first oxygen delivery tube and the second oxygen delivery tube in place across the patients face.

12. An apparatus for seeming a nasal cannula across a patient's face, the nasal cannula comprising a nasal insert, the apparatus comprising:
- a first oxygen delivery tube connected to the nasal canula and positionable on a first side of the patients face;
- a second oxygen delivery tube connected to the nasal cannula and positionable on a second side of the patient's face;
- a first oxygen delivery tube holder comprising a first portion comprising an elastic material, the elastic material being manipulable to be looped over the first oxygen delivery tube and being securable to itself via a snap fastener, wherein elastic material of the first oxygen delivery tube holder allows the first oxygen delivery tube holder to both slide along a length of the first oxygen delivery tube and accommodate varying diameters of the first oxygen delivery tube;
- a second oxygen delivery tube holder comprising a first portion comprising an elastic material, the elastic material being manipulable to be looped over the second oxygen delivery tube and being securable to itself via a snap fastener, the second oxygen delivery tube holder further comprising a second portion comprising an aperture, wherein elastic material of the second oxygen delivery tube holder allows the second oxygen delivery tube holder to both slide along a length of the second oxygen delivery tube and accommodate varying diameters of the second oxygen delivery tube; and
- a strap attached to the first oxygen delivery tube holder, the strap comprising a first portion comprising loop material and a second portion comprising complimentary hook material, the second oxygen delivery tube holder being securable to the first oxygen delivery tube holder by pulling the strap through the aperture in the second portion of the second oxygen delivery tube holder and attaching the second portion of the strap to the first portion of the strap using the complimentary hook and loop material.

* * * * *